(12) United States Patent
Snook et al.

(10) Patent No.: US 10,960,228 B2
(45) Date of Patent: Mar. 30, 2021

(54) ABSORBING DEVICE FOR RADIOTHERAPY

(71) Applicant: Medical Intelligence Medizintechnik GmbH, Schwabmunchen (DE)

(72) Inventors: Christopher Snook, Neusaess (DE); Ulrike Lutz, Landsberg (DE); Armin Fürst, Geltendorf (DE); Florian Weber, Freising (DE); Rui Liu, Augsburg (DE); Manfred Wiesmeier, Egenburg (DE)

(73) Assignee: Medical Intelligence Medizintechnik GmbH, Schwabmunchen (DE)

( * ) Notice: Subject to any disclaimer, the term of this patent is extended or adjusted under 35 U.S.C. 154(b) by 341 days.

(21) Appl. No.: 16/086,197

(22) PCT Filed: Mar. 20, 2017

(86) PCT No.: PCT/EP2017/056528
§ 371 (c)(1),
(2) Date: Sep. 18, 2018

(87) PCT Pub. No.: WO2017/162573
PCT Pub. Date: Sep. 28, 2017

(65) Prior Publication Data
US 2020/0215354 A1 Jul. 9, 2020

(30) Foreign Application Priority Data

Mar. 21, 2016 (GB) ..................................... 1604713

(51) Int. Cl.
*A61N 5/00* (2006.01)
*A61N 5/10* (2006.01)
*A47C 31/00* (2006.01)

(52) U.S. Cl.
CPC .......... *A61N 5/1049* (2013.01); *A47C 31/004* (2013.01); *A61N 2005/1051* (2013.01);
(Continued)

(58) Field of Classification Search
CPC ............................................. A61N 2005/1094
See application file for complete search history.

(56) References Cited

U.S. PATENT DOCUMENTS

| | | |
|---|---|---|
| 6,246,231 B1 | 6/2001 | Ashe |
| 2003/0011359 A1* | 1/2003 | Ashe ...................... A61B 5/062 |
| | | 324/207.17 |

(Continued)

FOREIGN PATENT DOCUMENTS

| | | |
|---|---|---|
| WO | WO-2006086802 A2 | 8/2006 |
| WO | WO-2008079071 A1 | 7/2008 |

OTHER PUBLICATIONS

"Flexible Absorbent Material (FAM)", Crown Ferrite, online [www.cfe.com.tw:80/2-absorber/crown-ferrite-absorber-flexible-absorbent-material-fam.pdf [retrieved Aug. 29, 2018], (Jan. 13, 2016), 14 pgs.

(Continued)

*Primary Examiner* — Dani Fox
(74) *Attorney, Agent, or Firm* — Schwegman Lundberg & Woessner, P.A.

(57) ABSTRACT

An absorbing device (24, 24', 24", 41) for radiotherapy treatment comprising at least one layer of electromagnetic absorbing material wherein the absorbing material is for preventing interaction between a target localisation system (1) having a targeted frequency range of between about 300 kHz and 500 kHz and a treatment table (4).

14 Claims, 10 Drawing Sheets

(52) U.S. Cl.
CPC ............... *A61N 2005/1063* (2013.01); *A61N 2005/1094* (2013.01)

(56) References Cited

U.S. PATENT DOCUMENTS

2013/0078414 A1   3/2013   Coppens et al.
2015/0223904 A1   8/2015   Iustin et al.

OTHER PUBLICATIONS

"High Flux Density Mn—Zn Ferrite MN67", Ceramic Magnetics, Inc.: A National Magnetics Group Company, online [hhttp://www.cmi-ferrite.com/Materials/Datasheets/MnZn/MN67.pdf] [retrieved Aug. 29, 2018], (Jan. 23, 2013), 2 pgs.

"International Application Serial No. PCT/EP2017/056528 , International Preliminary Report on Patentability dated Jun. 14, 2018", (dated Jun. 14, 2018), 15 pgs.

"International Application Serial No. PCT/EP2017/056528 , International Search Report dated Aug. 2, 2017", (dated Aug. 2, 2017), 4 pgs.

"International Application Serial No. PCT/EP2017/056528 , Written Opinion dated Aug. 2, 2017", (dated Aug. 2, 2017), 5 pgs.

Ahuir, Jorge Victoria, "Going Wireless with Magnetic Shielding", Wurth Elektronik, [online] http://www.mouser.com/pdfDocs/Wurth-Going-Wireless-with-Magnetic-Shielding.pdf [retrieved Aug. 29, 2018], (Oct. 15, 2013), 10 pgs.

"Chinese Application Serial No. 201780018663.8, Office Action dated Nov. 18, 2020", w/ English Translation, (dated Nov. 18, 2020), 10 pgs.

\* cited by examiner

ABSORBING DEVICE FOR RADIOTHERAPY

PRIORITY APPLICATIONS

This application is a U.S. National Stage Filing under 35 U.S.C. 371 from International Application No. PCT/EP2017/056528, filed on Mar. 20, 2017, and published as WO2017/162573 on Sep. 28, 2017, which claims the benefit of priority to United Kingdom Application No. 1604713.6, filed on Mar. 21, 2016; the benefit of priority of each of which is hereby claimed herein, and which applications and publication are hereby incorporated herein by reference in their entirety.

The present invention relates to an absorbing device for use in patient imaging and radiotherapy treatment, in particular to an absorbing device for use with electromagnetic target localisation systems.

An increasing number of applications in radiation therapy utilise tumour-tracking technologies. The use of radio frequency and similar electromagnetic technology for tumour tracking depends strongly on the recording of correct positional information.

Following determination of tumour location using an imaging system (X-ray, CT, MRI, ultrasound etc.), tumour-tracking technology is used to re-align radiation therapy treatment. Target localisation systems, comprising a target localisation antenna and one or more target transponders, are becoming increasingly common in radiotherapy treatments. It is understood in the field of the present invention that transponders are also referred to as beacons or markers. The transceiver of a localisation antenna generates an alternating electromagnetic field, excites implanted beacons/markers close to the target, and receives a return signal from the beacons/markers from which positional information is derived. In radiotherapy treatment using a target localisation system, the machine isocentre is aligned with the treatment target prior to treatment beginning. The accuracy of the subsequent treatment will depend on the accuracy of this alignment. Furthermore, target localisation systems are also used to detect even slight movement of the patient/target during treatment so that the isocentre can be re-aligned and dynamically adjusted if necessary, to maintain the accuracy of the radiation treatment. Accurate target localisation enables more effective treatment, minimises any potential harm to surrounding healthy tissue and any potential side effects of the treatment.

Most modern linear accelerators (LINAC) are equipped with a motorised gantry and a motorised treatment table. The treatment table is commonly equipped with a carbon fibre couch-top due to the high degree of stability and yet low X-ray attenuation of the material, which minimises artefacts on X-ray images acquired during treatment and optimises dose dosimetry properties, such as low X-ray attenuation and dose build up.

However, both the carbon couch top and the metal parts of the gantry are electrically conductive. The transceiver of a localisation system is positioned close to the gantry and to the treatment table. It has been found that part of the alternating magnetic energy is transferred to circular current on the surface of the conductive materials and is eventually dissipated as heat. Consequently, the wireless transponders/beacons/markers of a localisation system receive less energy than previously such that they do not excite to the desired extent. This results in localisation errors and a shorter communication distance between the wireless transponders/beacons/markers and the transceiver. Furthermore, other surrounding electronics; for example, motor drivers from the gantry and the treatment table, can also generate electromagnetic noise, which interferes with the signal detected by the transceiver and reduces localisation accuracy.

Existing couch tops used with electromagnetic tumour tracking make use of a non-standard carbon couch top to prevent the above-described, non-systematic errors in the position measurement occurring. US patent publication US20130078414 discloses such a carbon couch top with non-standard carbon fibre routings. The manufacture of such a non-standard couch top is complex because of the need to align each fibre element both vertically and horizontally. This complexity means that the product is very expensive; the rigidity and the loading capability of the couch top is reduced. Therefore, there remains a need to be able to use an electromagnetic target localisation system with linear accelerators having a conventional carbon-fibre couch top.

US patent U.S. Pat. No. 6,246,231 discloses a magnetic field position and orientation measurement system comprising a transponder implanted into the body, which is used in surgical and diagnostic treatments. A transmitter and a permeable layer attached to the rear side thereof are used to avoid the surrounding metallic distortion and reduction of magnetic field strength. Both the transmitter and the permeable layer are mounted on the aluminium surgical table. The receiver is implanted and powered via a cable connection. US patent publication US2015/0223904 discloses a positioning device for tracking a radiofrequency positioning device, which is also implanted within a body and powered via a cable connection.

Such prior art systems disclose that a patient having an implanted beacon/transmitter lies on a patient-support table that is conductive. A main antenna assembly rests on the table and a barrier sheet is placed between the patient-support table and the antenna. However, such existing arrangements have not solved the practical problems associated with the use of existing electromagnetic/wireless beacon systems and conductive patient support table used in radiotherapy apparatus; for example, problems associated with the eddy currents generated by the transceiver; electronic noise from the motor inside the patient support system; unexpected radiation activity effects; dose dosimetry changes and X-ray image artefacts. Furthermore, such known systems do not allow the localization system to be a separate, self-contained system, but require a connection to the patient support system; that is, the implanted transponders/beacons/markers inside the patient's body are not self-powered but rather need additional power cable connections.

It is, therefore, an object of the present invention to seek to alleviate the above-identified problems.

SUMMARY OF THE INVENTION

According to one aspect of the present invention, there is provided an absorbing device for radiotherapy treatment comprising at least one layer of an electromagnetic radiation absorbing material, wherein the absorbing material is for preventing interaction between a target localisation system having a targeted frequency range of between about 300 kHz and about 500 kHz and a conductive treatment table Preferably, the absorbing device prevents interaction between the target localisation system and the conductive treatment couch without introducing significant radiation activity and X-Ray artefacts.

The present invention minimises or prevents interaction between the electrically conductive material of the couch top and the target wireless beacons (transponders/markers) of the localisation system to ensure that accurate target localisation and so accurate radiotherapy treatment is achieved. The present invention allows for the use of known electromagnetic target localisation systems with existing carbon-fibre couch tops. The present invention prevents tracking errors with localisation systems in which the transceiver antenna generates a very high alternating electromagnetic field. The implanted wireless beacon is directly powered by such alternating electromagnetic fields without using an additional energy source, such as a battery. Once the wireless beacon is sufficiently excited by the alternating electromagnetic field, it sends a return signal to the transceiver antenna of the localisation system.

It has been found that magnetic flux is not continuous when it meets with the conductive couch top and a portion of the alternating magnetic field transfers to a circular flow (e.g. as so called "eddy currents") on the surface of the conductive treatment table, which eventually is dissipated as heat. It has also been found that such circular currents are generated not only by the carbon couch top, but also from other surrounding conductive materials; for example from the LINAC gantry. Without the specific arrangement of the present invention, the wireless beacon receives less energy than before and cannot excite properly, which results in localization errors and a shorter communication distance with respect to the transceiver of a localisation system.

Preferably, the absorbing device comprises a material having high magnetic permeability.

A material having high magnetic permeability absorbs the generated electromagnetic field from localisation systems before it reaches the carbon-fibre couch top and partially dissipated as heat.

Preferably, the absorbing device comprises a material having a real part of relative magnetic permeability ($\mu'$) of about 230 at 300 kHz; preferably, having a real part of relative magnetic permeability of between about 175-285 at 300 kHz; optionally, having a real part of relative magnetic permeability of between about 150-310 at 300 kHz. Alternatively, the absorbing device comprises a material having a real part of relative magnetic permeability of about 450 at 300 kHz; optionally, having a real part of relative magnetic permeability of between 450-690 at 300 kHz.

Preferably, the absorbing device comprises a material having low surface conductivity.

A material having low surface conductivity provides a significant resistance to current running along the surface of the absorber device.

Preferably, the surface resistance is greater than or equal to about 1.00E+09 Ohms.

Preferably, the absorbing device comprises at least one ferrite layer, wherein the or each ferrite layer comprises a plurality of ferrite sheets; wherein each ferrite sheet has a thickness of between about 0.05 mm and about 1 mm.

Ferrite materials are commonly ferromagnetic ceramic compounds and are hard and brittle. Thus, there is considerable difficulty in achieving a layer having a large size and uniform thickness. The present invention uses a plurality of ferrite sheets to overcome these disadvantages.

More preferably, the plurality of ferrite sheets are stacked and held together with an adhesive; optionally, the plurality of ferrite sheets are stacked and held together with an adhesive tape.

The ferrite materials used in preferred embodiments of the present invention have a fixed density and it has been found that the dose dosimetry will change significantly with a very thick ferrite layer. Moreover, high-density and the use of a thick ferrite layer can also generate unwanted radio activation. The safety issues associated with these changes have been carefully considered to arrive at the thickness and the laminar, stacked configuration of the present invention, which allows for a safe and cost-effective way to provide the absorbing device.

Real time tumour tracking systems can generate a very high magnetic field and the use of a single ferrite layer would not be sufficient because a single ferrite layer will be "saturated", i.e. the magnetic flux would exceed the absorbing capabilities of the ferrite layer. The multi-layer ferrite sheet of the present invention increases the effective "storage capacity" of the absorbing device to avoid magnetic flux saturation. Furthermore, the present invention overcomes potential difficulties in forming a ferrite layer from a material which is inherently brittle.

Furthermore, the ferrite layer reduces the risk of disturbance caused by electronic noise; for example, electronic noise created by the motor drive inside the treatment table. Thus, the tracking accuracy is improved and the potential for increasing the distance between the beacon and the transceiver can be increased, which enables accuracy to be maintained for larger patient sizes.

Preferably, the size of each ferrite layer covers the transceiver antenna size of the target localisation system. More preferably, the or each ferrite layer covers the treatment table.

The size of the or each ferrite layer of the absorbing device is carefully selected to ensure that electronic noise generated from the motor of the table movement mechanism is limited. Furthermore, by covering the size of the transceiver antenna, if not the entire treatment table, the present invention ensures that the effect of eddy currents or electronic noise from the gantry, when it rotates underneath the treatment table, is minimised. Thus, by use of the present invention, the target localisation system is robust for long distance usage, i.e. when there is a greater distance for wireless communication between the beacon and transceiver antenna of the target localisation system; for example, for treatment of larger patients.

Preferably, the absorbing device comprises at least one layer of a ferrite material; preferably, a sintered ferrite material; more preferably, a sintered sheet of a ferrite material.

Preferably, the absorbing device comprises a material having a real part of relative permeability ($\mu'$) greater than 200 at 300 kHz and an imaginary part of relative permeability ($\mu''$) less than 50 at 300 kHz.

Preferably, the absorbing device comprises a plurality of overlapping sheets of radiofrequency radiation absorbing material.

Preferably, the absorbing device comprises at least one spacer layer.

Preferably, the or each spacer layer comprises a material/s, such as epoxy, polyester, polymer, polymethacrylimide, vinyl ester resin, wood, ceramic, aramid, glass fibre or ultrahigh molecular weight polyethylene.

The plurality of ferrite sheets used to form the laminar ferrite layer of the absorbing device has an impact on the radiation activity, dose, and X-ray/CT imaging quality. For example, the laminar ferrite layer can generate artefacts on the CT image. The use of at least one spacer or buffer layer; preferably, positioned above the ferrite layer, avoids the risk of inducing radiation activity and also ensures that the high quality of CT imaging can be maintained. Thus, the present invention reduces the potential for the ferrite material to introduce radiation activation, dose dosimetry changes, or X-ray imaging artefacts.

Preferably, the absorbing device comprises at least one electrical insulating layer.

Preferably, the absorbing device will be substantially at least about 95% transparent to X-ray radiation.

Preferably, the absorbing device is substantially transparent to X-ray radiation.

This is a particularly advantageous feature of the present invention because the absorber layer has a negligible effect on X-ray radiation. In this respect, it has been shown that the effect on X-ray radiation is no more than about 1-2%.

Within this specification, the term "substantially transparent to X-ray radiation" means that at least about 90%, preferably at least about 95%, preferably at least about 97%, preferably at least about 98%, preferably at least about 99%, preferably substantially all, preferably all X-ray radiation passes through the absorbing device.

Preferably, at least about 50% of the total mass of the or each ferrite layer comprises iron oxide ($Fe_2O_3$).

Preferably, the absorbing device comprises at least one ferrite layer comprising nickel oxide (NiO) and/or zinc oxide (ZnO) and/or copper oxide (CuO) and/or iron oxide ($Fe_2O_3$).

Preferably, the or each ferrite layer has a surface resistance greater than about 1.00 E+0.9 Ohms.

Preferably, the absorbing device is configured to be positioned, in use, between a patient and the treatment table.

In another aspect of the present invention, there is provided a mattress for radiotherapy treatment comprising an absorbing device having at least one layer of a radiofrequency absorbing material for preventing interaction between a target localisation system and a treatment table, wherein the localisation system is for a targeted frequency range of between about 300 kHz and 500 kHz.

An absorbing layer used for radiotherapy applications is exposed to a high-energy electron beam from the LINAC and so safety issues need to be addressed. The particular material composition of the present invention ensures that the mattress/absorbing device placed between the patient and the treatment table meets the necessary safety standards.

In another aspect of the present invention, there is provided a patient positioning device for radiotherapy treatment comprising an absorbing device having at least one layer of a radiofrequency absorbing material for preventing interaction between a target localisation system having a targeted frequency range of between about 300 kHz and 500 kHz and a conductive treatment table.

In another aspect of the present invention, there is provided a couch top for patient support during radiotherapy treatment comprising an absorbing device as previously described.

In another aspect of the present invention, there is provided a tumour localisation system comprising at least one wireless beacon, at least one transceiver and an absorbing device as previously described; wherein the at least one wireless beacon is implantable within a patient and the at least one transceiver is for placing on or above a patient.

The localisation system of the present invention enables the transceiver, in use, to be placed on top of the patient's body and so away from the treatment table; for example, about 6 cm to 27 cm away from the conductive surface. This allows for a large range of patient sizes.

In a further aspect of the present invention, there is provided a mattress for radiotherapy treatment comprising an absorbing device as previously described.

In a further aspect of the present invention, there is provided an absorbing device for positioning around a patient. Preferably, wherein the absorbing device comprises at least two substantially upstanding walls and at least one transverse member therebetween for positioning over and around a patient.

According to a further aspect of the present invention, there is provided an absorbing device for radiotherapy treatment comprising at least one layer of a radiofrequency radiation absorbing material, wherein the absorbing material is for preventing interaction between a target localisation system and a treatment table.

Preferably, the absorbing device comprises a material having high magnetic permeability.

Preferably, the absorbing device comprises a material having low surface conductivity.

Preferably, the absorbing device comprises a material having a relative magnetic permeability of about 230; preferably, having a relative magnetic permeability of between about 175-285; optionally, having a relative magnetic permeability of between about 150-310. Alternatively, the absorbing device comprises a material having a relative magnetic permeability of about 450; optionally, having a relative magnetic permeability of between 450-690.

More preferably, the absorbing device comprises a material having a relative magnetic permeability of about 230 and thickness of about 0.3 mm.

Preferably, the product of relative magnetic permeability and thickness of the absorbing device is between about 60 mm and about 80 mm; more preferably, the product of relative magnetic permeability and thickness of the absorbing device is between about 65 mm and about 75 mm; still more preferably, the product of relative magnetic permeability and thickness of the absorbing device is about 70 mm; most preferably, the product of relative magnetic permeability and thickness of the absorbing device is about 69 mm.

Preferably, the absorbing device comprises a material having a surface resistivity greater than or equal to about 1.00 E+09 Ohms.

Preferably, the absorbing device comprises at least one layer of a ferrite material; preferably, a sintered ferrite material; more preferably, a sintered sheet of a ferrite material.

Preferably, the absorbing device comprises at least one layer of Crown Ferrite FAM8; more preferably, at least one layer of Crown Ferrite FAM8 having a thickness of between about 0.1 mm and about 0.4 mm; most preferably, having a thickness of about 0.33 mm.

Preferably, the absorbing device comprises at least one layer of Würth Elektronik WE-FSFS 354003; preferably having a thickness of between about 0.2 mm-0.4 mm; more preferably, having a thickness of about 0.3 mm.

Preferably, the absorbing device comprises a plurality of overlapping sheets of radiofrequency radiation absorbing material.

Preferably, the absorbing device comprises at least one reinforcing layer.

Preferably, the absorbing device comprises at least one spacer layer.

Preferably, the absorbing device comprises at least one electrical insulating layer.

Preferably, the absorbing device will be substantially at least about 95% transparent to X-ray radiation.

Preferably, the absorbing device is substantially transparent to X-ray radiation.

Preferably, the absorbing device is configured to be positioned, in use, between a patient and the treatment table.

In another aspect of the present invention, there is provided a mattress for radiotherapy treatment comprising an absorbing device having at least one layer of a radiofrequency radiation absorbing material for preventing interaction between a target localisation system and a treatment table.

Within this specification embodiments have been described in a way which enables a clear and concise specification to be written, but it is intended and will be appreciated that embodiments may be variously combined or separated without parting from the invention.

Within this specification, the term "about" means plus or minus 20%, more preferably plus or minus 10%, even more preferably plus or minus 5%, most preferably plus or minus 2%.

DETAILED DESCRIPTION

Example embodiments of the present invention will now be described with reference to the accompanying figures, in which.

Figure 8A:
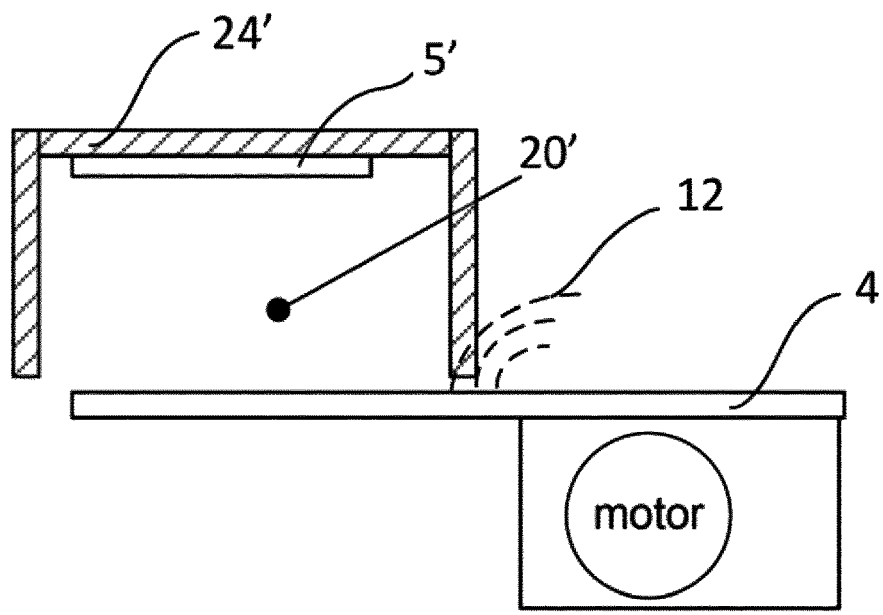
Figure 8B:
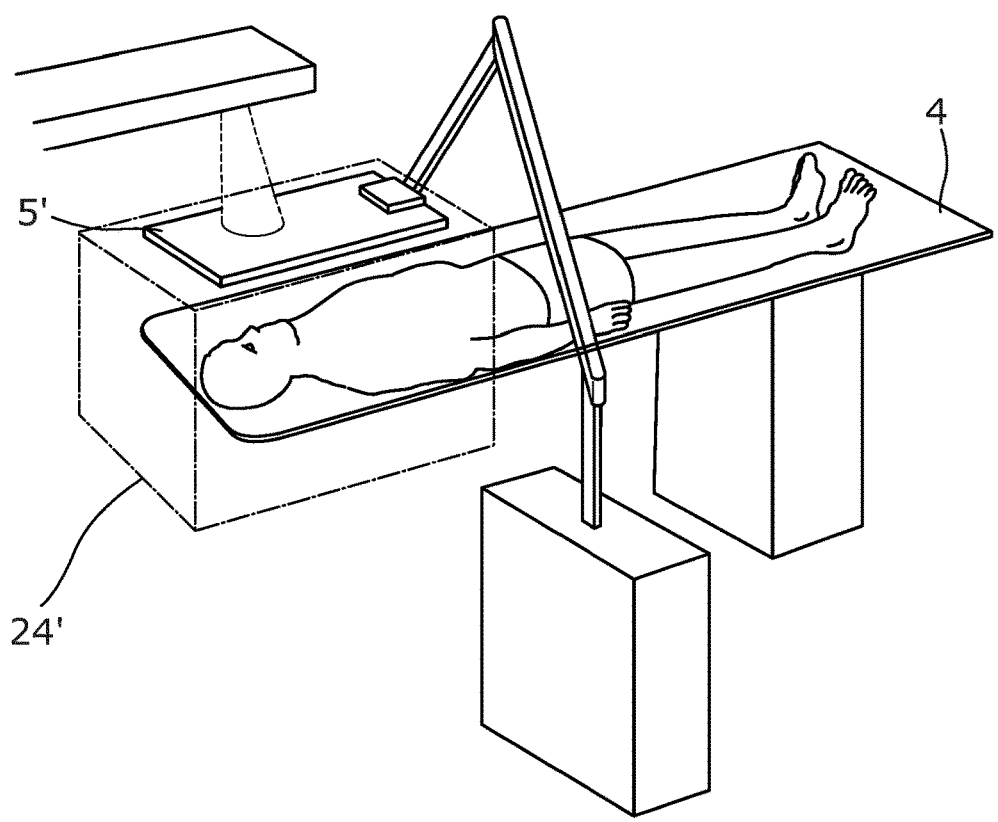
Figure 8C:
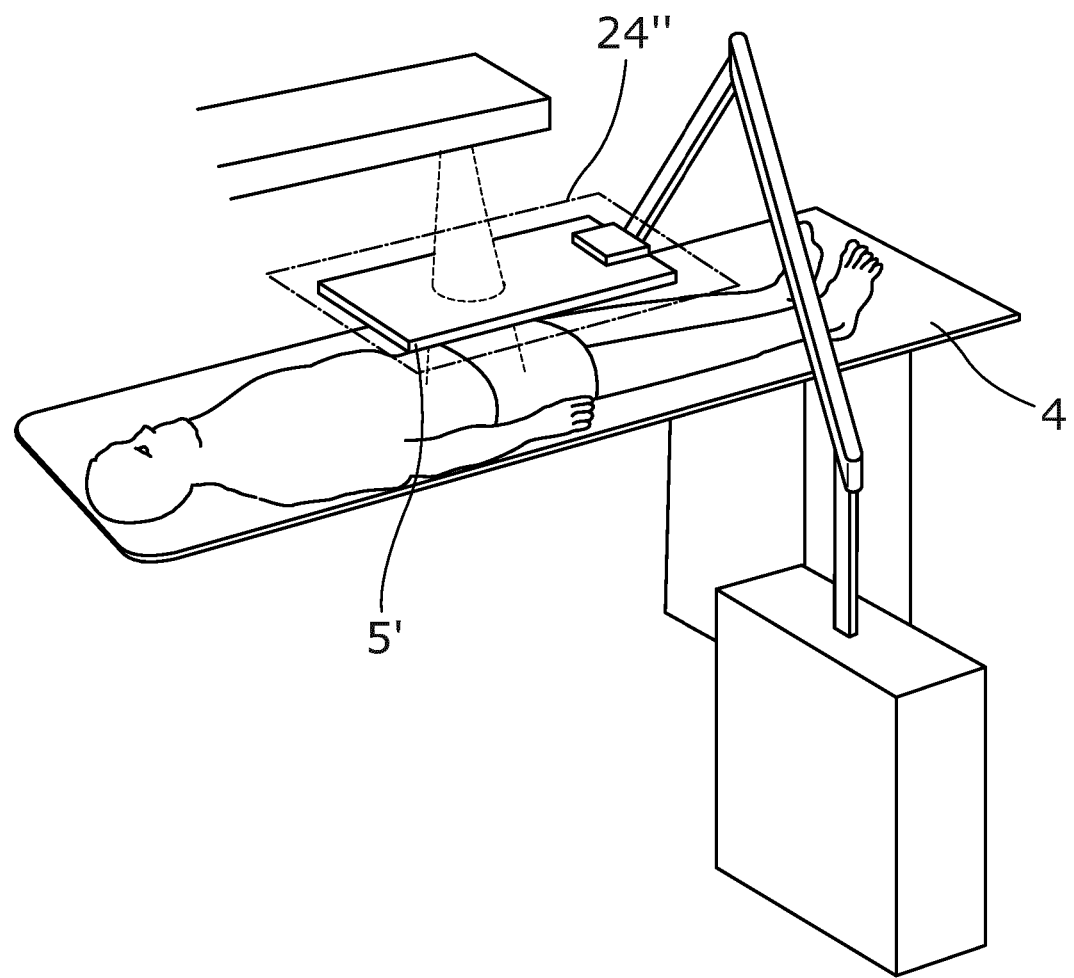
Figure 9A:
Figure 9B:
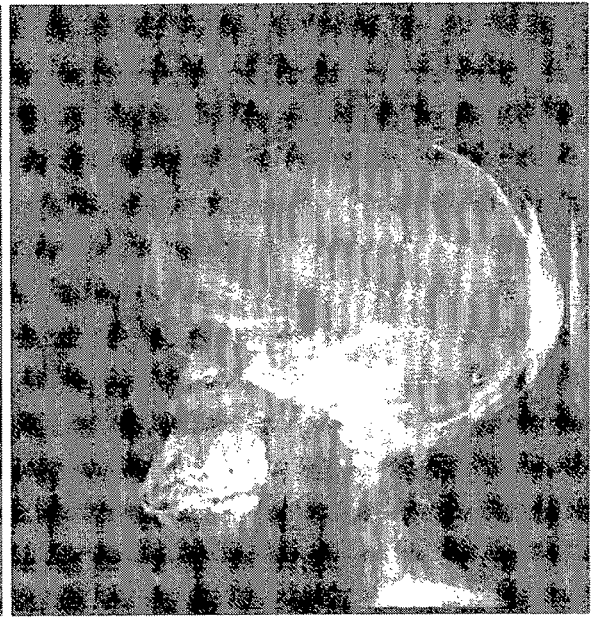
Figure 9C:
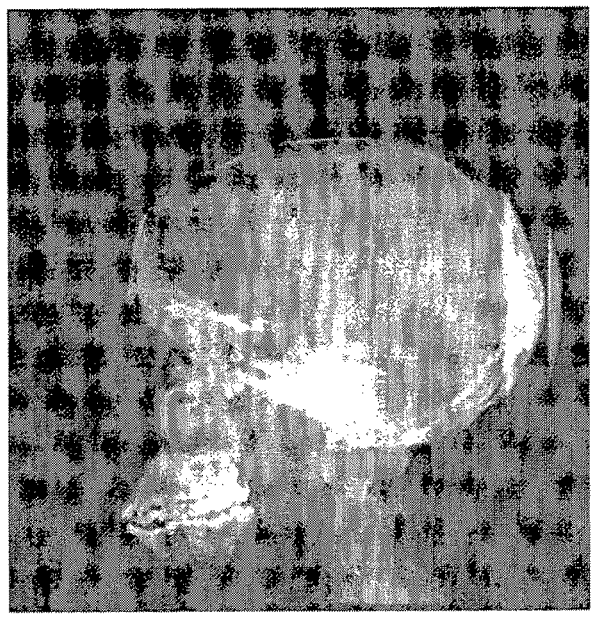
Figure 9D:
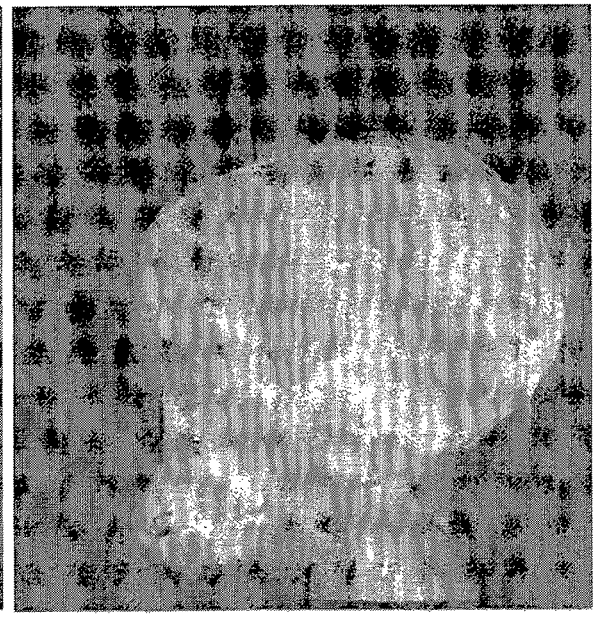

FIG. 8a, FIG. 8b, and FIG. 8c show further alternative embodiments of the absorbing device of the present invention.

FIGS. 9a, 9b, 9c and 9d illustrate the introduced X-ray artefacts on a head phantom with different ferrite samples.

Figure 10A:
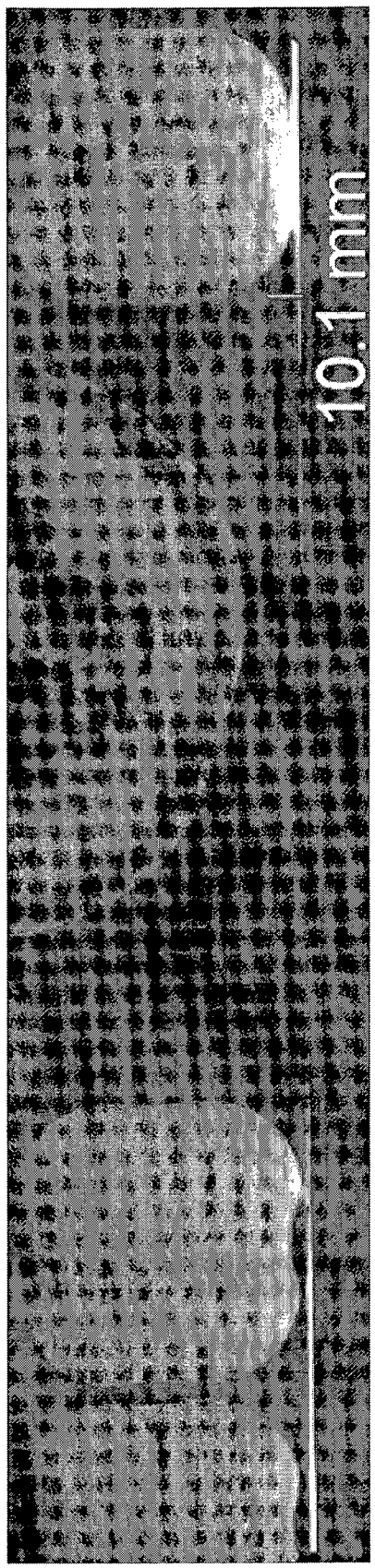
Figure 10B:
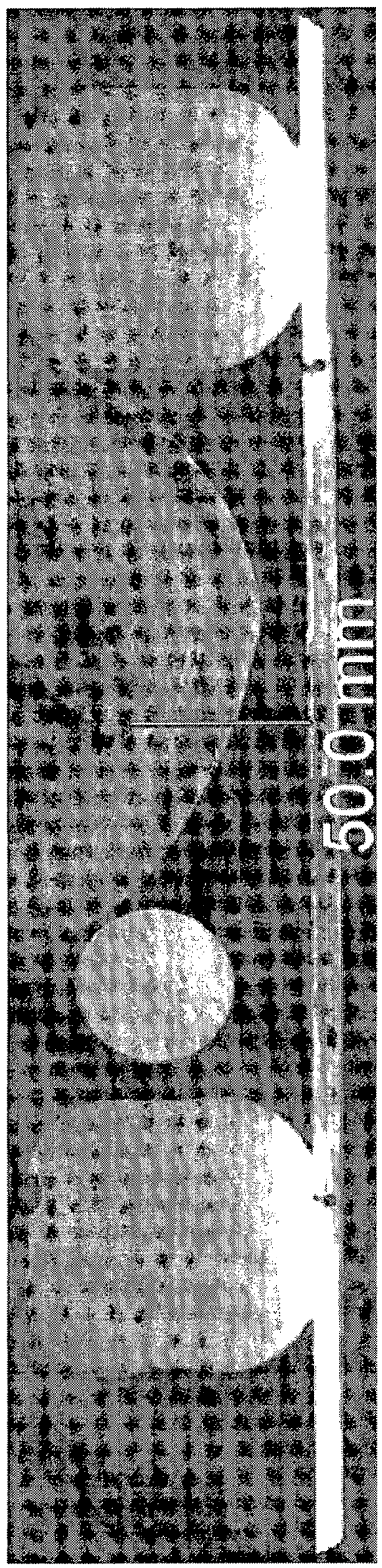

FIGS. 10a and 10b illustrates of the X-ray artefacts with multi-layer ferrite panels: (a) single layer ferrite panel; (b) five-layer ferrite panels.

The present invention is intended to support the use of an electromagnetic tumour tracking system in combination with a carbon-fibre couch top in radiation imaging and therapy.

Figure 1:
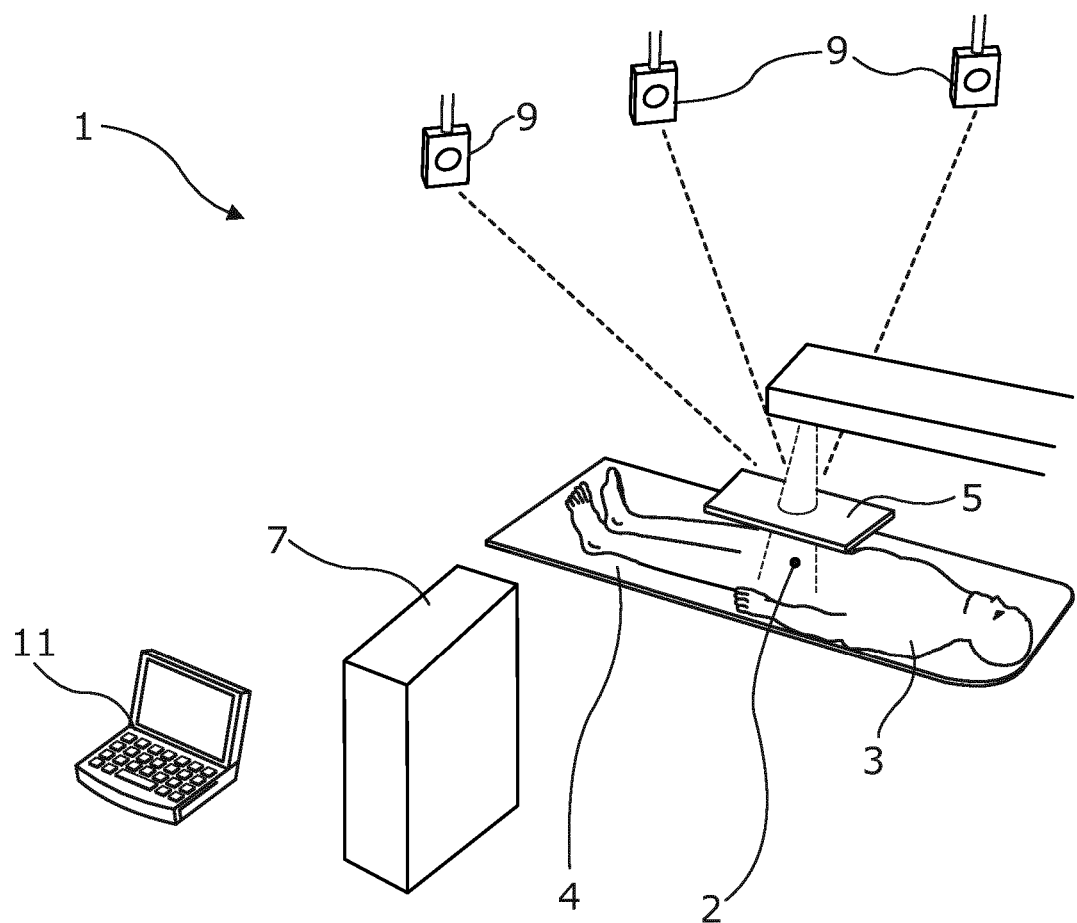
FIG. 1 shows a side view of an example treatment room set up for a localisation system, with which the device of the present invention is configured to be used.

Referring to FIG. 1, a target localisation system 1 for use during radiation therapy is shown. A plurality of wireless beacons 2 are implanted into the patient 3; for example, the wireless beacons 2 (also known as markers or transponders) are implanted at or near the treatment target. Alternatively, or in addition, a plurality of wireless beacons 2 are placed on the surface of the patient's skin, with the patient 3 lying on the treatment table/couch top 4. The wireless beacons 2 send signals of target motion in real time during treatment. An array of transceivers 5, often in the form of a plate, which are used to transmit, detect and measure the beacon transponder signals to enable the calculation of an objective measurement of the location of the treatment target in three dimensions. As shown in FIG. 1, in use the transceiver antenna 5 is above the patient 3 and the couch top 4 is below the patient, with the wireless beacons 2 placed between the transceiver 5 and the couch top 4.

Accurate localisation of the target means that the radiation therapist can align the patient's treatment target to the machine isocentre before radiation treatment commences. The use of the wireless beacons 2 and the transceiver 5 also allows for real time monitoring of the patient/target movement during radiotherapy treatment delivery. It is to be understood that the example shown in FIG. 1 comprises an array 5 of electromagnetic transceivers; however, in alternative embodiments of the present invention, the target localisation system comprises separate components to transmit and receive localisation signals.

In a preferred embodiment of the present invention, the or each radiofrequency beacon 2 is wireless and does not require a battery. The beacon transponders 2 are self-powered by the magnetic field of the transceiver antenna.

Referring to FIG. 1, a typical target localisation system 1 further comprises a console 7 to which the electromagnetic transceiver 5 is attached; an optical system 9, for example comprising a plurality of infrared cameras; and a tracking station 11, from where a radiation therapist or similar health professional will monitor set-up and treatment of the patient 3. In use, a radiation treatment device includes a linear accelerator (LINAC) and a movable gantry, which is powered by a motor (not shown). The treatment delivered to the patient is adjusted in real time according to the detected 3D position of the patient 3, which is given by the target localisation system 1.

Figure 2A:
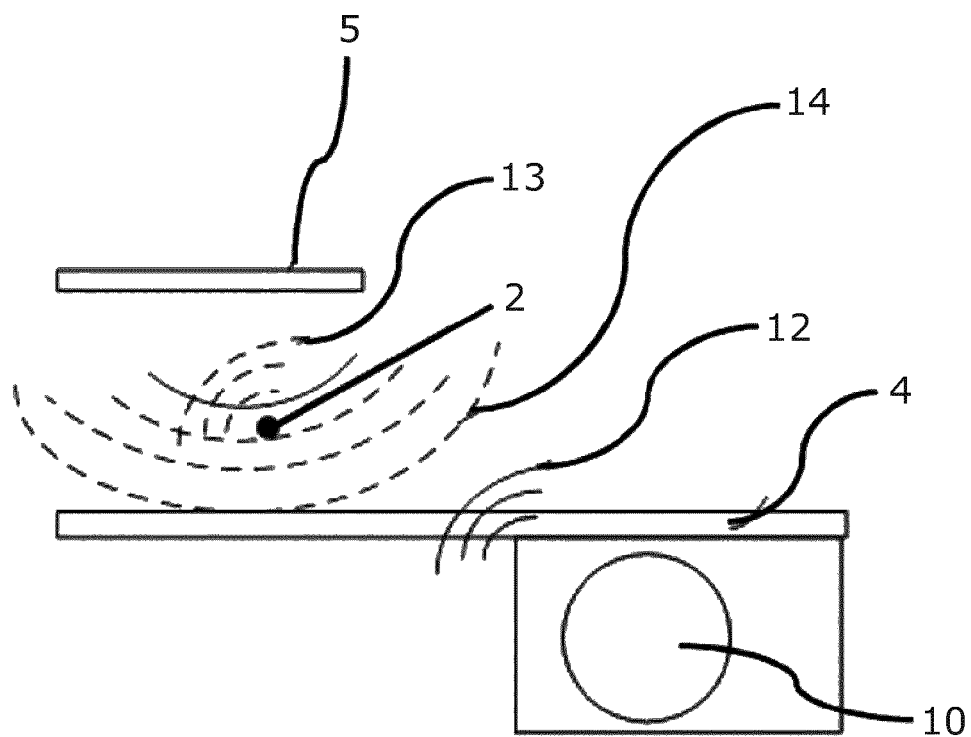
FIG. 2a is a schematic of the response signals from a wireless beacon used in a localisation system without the device of the present invention.

Referring to FIG. 2a, the transceiver 5 of the localisation system generates a very high electromagnetic field and is placed on top of the patient's body with the patient (not shown) lying on top of the treatment table 4. The wireless beacon 2 is implanted into the patient's body or is placed on the patient's skin. The wireless beacon 2 is self-powered by the electromagnetic field generated from the transceiver 5 and does not have a battery or cable connection. The transceiver 5 and the wireless beacon 2 operate in a frequency range of between about 300 kHz and 500 kHz. FIG. 2a illustrates how the signal 13 from the wireless beacon 2 can be affected by surrounding electromagnetic noise that is generated; for example, by the motor 10 inside the treatment table, or from the LINAC gantry (not shown). This results in localisation errors. Furthermore, as shown in FIG. 2a, the electromagnetic field from the transceiver 5 travels towards the conductive couch top 4 and the LINAC gantry (not shown), such that part of the alternating electromagnetic field is transferred to a circular current at the surface of the conductive materials, which is then eventually dissipated as heat. Thus, the wireless beacon 40 receives less electromagnetic energy and may be unable to generate sufficient feedback signals, which results in localisation errors because of an incorrect calculation of the objective measurement of the location of the treatment target in three dimensions.

Unless explicitly specified to the contrary, is to be understood that the term "permeability" refers to the real part of relative permeability μ', in the context of the present invention.

It is to be understood that, in the context of the present invention, "high" permeability refers to the real part of relative permeability (μ') being greater than 200 at 300 kHz, with a preferred range between 200 and 1000 at 300 kHz. It is to be understood that, in the context of this invention, "low" loss refers to the imaginary part of relative permeability ($\mu''$) being less than 50 at 300 kHz, with a preferred range between 1 and 50 at 300 kHz.

The material selected for the absorbing device 24 of the present invention was selected to achieve optimum localisation accuracy. It was found that a material having high relative magnetic permeability was well-suited to the present invention. Relative permeability $\mu$ is a complex number and contains both a real part ($\mu'$) and an imaginary part ($\mu''$) as expressed in Equation 1:

$$\mu = \mu' - j\mu'' \quad \text{[Equation 1]}$$

The real part $\mu'$ refers to the storage capability of the electromagnetic energy and the imaginary part $\mu''$ refers to the loss behaviour of the electromagnetic energy. Unless explicitly specified to the contrary, the term "permeability" refers to the real part of relative permeability $\mu'$, in the context of the present invention. The ideal material for use in the absorbing device 24 comprises a high storage capability ($\mu'$) and preserves electromagnetic energy with a low loss component ($\mu''$).

Figure 2B:
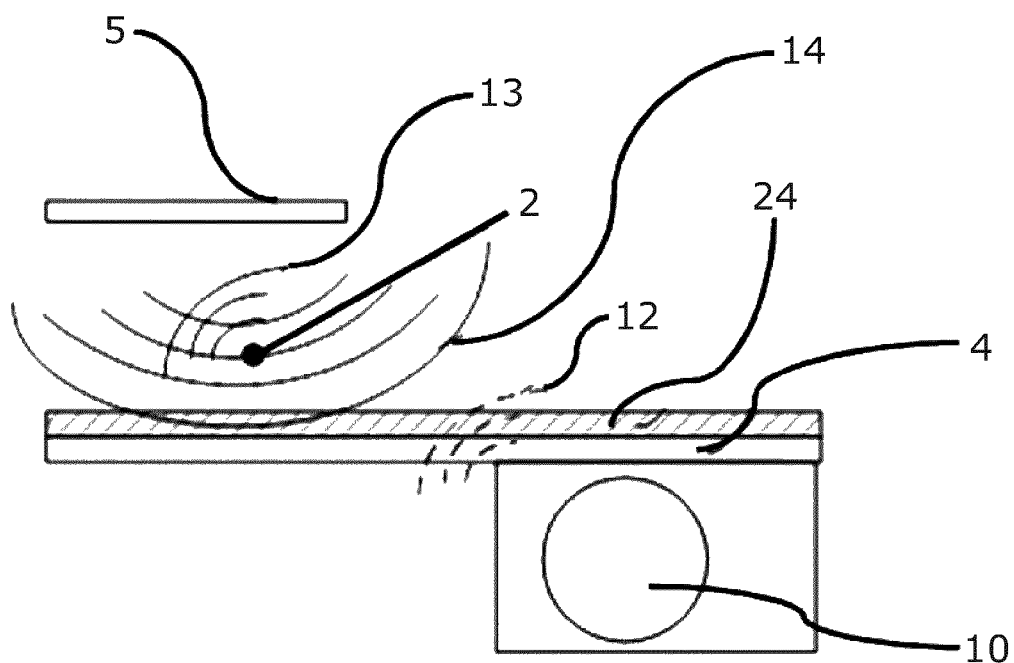
FIG. 2b is a schematic of the response signals from a wireless beacon used in a localisation system with the device of the present invention.

As shown in FIG. 2b, in a preferred embodiment of the present invention, the absorbing device 24 is placed on top of the couch top 4, on which the patient lies, with the transceiver 5 above the patient. Thus, the magnetic flux 14 of the electromagnetic field 14 generated from the transceiver 5 will be absorbed inside the absorber layer within the absorbing device 24, rather than being dissipated at the surface of the conductive couch top 4, as shown in FIG. 2a. With the improvement of the present invention, the wireless beacon 2 receives sufficient electromagnetic energy from the transceiver to send feedback (localisation) signals with sufficient strength for accurate localisation. Electromagnetic noise generated from the motor 10 will be absorbed locally and will be highly attenuated before reaching the wireless beacon 2. Thus, the wireless beacon 2 is significantly less affected by the surrounding conductive materials and electromagnetic noise, which significantly improves target localisation accuracy.

Various materials were investigated for the absorbing device of the present invention and the localisation errors were quantified for each possible material. Referring to FIG. 3b, the error (shown on the y-axis) was mainly found to be a localisation error in the z-direction, i.e. in the detected distance between the couch top 4 surface and the wireless beacons 2. With reference to FIG. 1, the wireless beacons 2 were mounted at a position with constant distance to the transceiver 5 and the couch top 4 was moved vertically.

Figure 3:
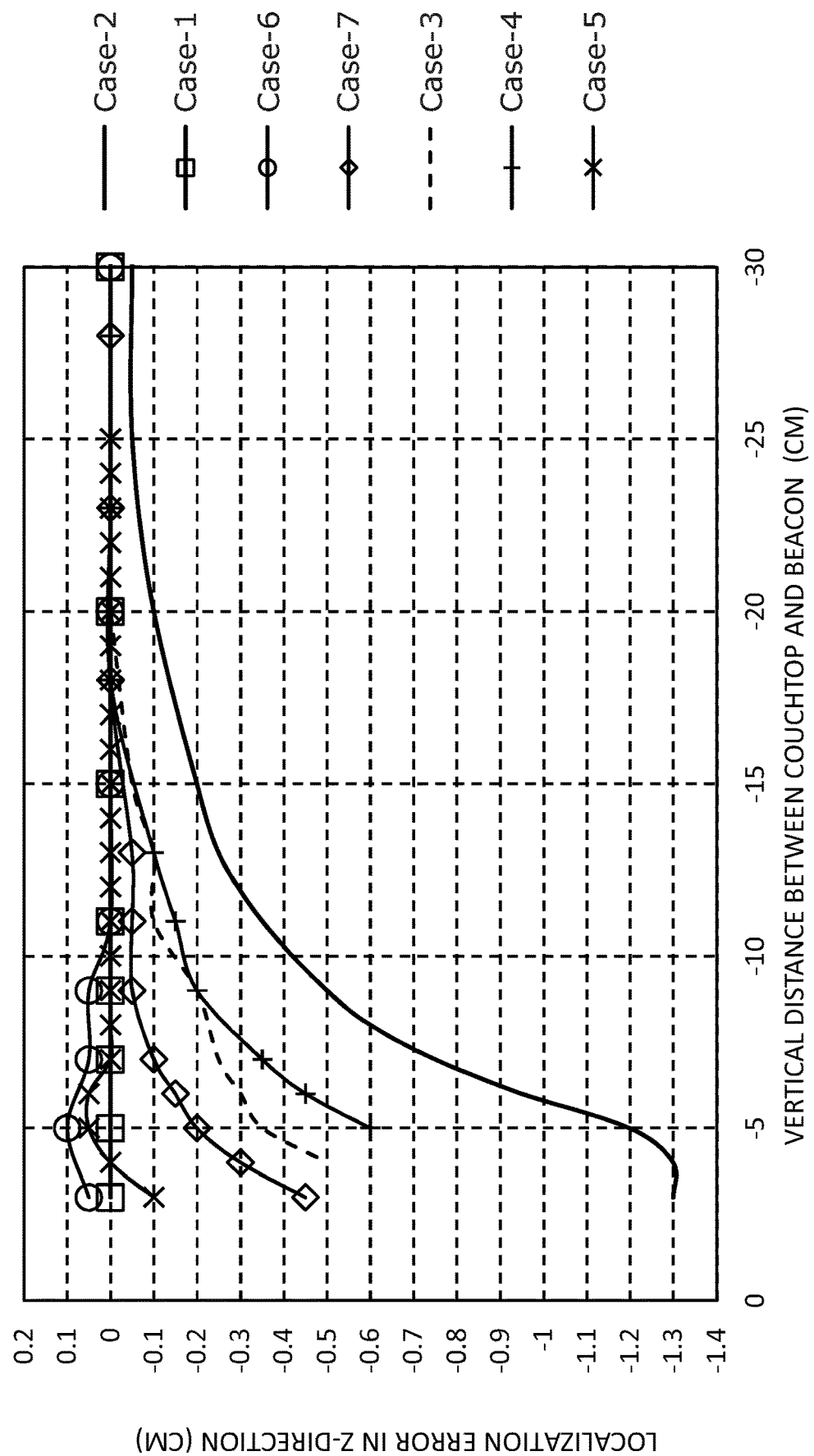
FIG. 3 is a graph showing the localisation error (y-axis) in the z-direction (cm) plotted against the vertical distance between the couch top and the beacon wireless beacon (x-axis) for various absorber materials.

The quantitative analysis to arrive at the results shown in FIG. 3 used a dedicated measurement test set-up to evaluate the localisation error for different absorber/layer configurations. The distance between the transceiver and the wireless beacon of the localisation system is fixed and the distance between the moveable couch top and the absorber layer was varied for a range of vertical positions. The localisation error with respect to the known position of the wireless beacon was recorded each time. Measurements were taken without the use of an absorber layer for comparison purposes.

The preferred material for use in the present invention has a high storage capacity (e.g. $\mu'$ is high) and a low loss behaviour (e.g. $\mu''$ is low) because this minimises the electromagnetic localisation error. It has also been found that the surface resistance of the absorber layer also affects the electromagnetic field and so the localisation accuracy.

It is to be understood that in the context of the present invention, the term "permeability" refers to the real part of relative permeability ($\mu'$) and the term "permeable materials" are the materials with a high real part of relative permeability ($\mu'$) value. Both $\mu'$ and $\mu''$ are strongly dependent on the frequency of the electromagnetic field. FIG. 3 relates to testing of the absorber layer of the present invention in respect of a variety of absorber layers and measurements were also taken without the use of an absorber layer for comparison purposes. The materials and couch top combinations that are shown on FIG. 3 are:

Case 1: non-conducting couch top;
Case 2: conductive couch top without using absorber layer;
Case 3: absorber layer with magnetically conducting nickel-iron alloy, also known as a p-metal, having a thickness of 0.1 mm, $\mu'>800$ at 300 kHz;
Case 4: absorber layer with magnetic powder and rubber, having a thickness of 2.5 mm, $\mu'=25$ at 300 kHz and $\mu''<3$ at 300 kHz;
Case 5: absorber layer with sintered ferrite panel, having a thickness of 0.2 mm, $\mu\infty=600$ at 300 kHz and $\mu''=220$ at 300 kHz;
Case 6: absorber layer with sintered ferrite panel, having a thickness of 0.2 mm, $\mu'=450$ at 300 kHz and $\mu''<30$ at 300 kHz;
Case 7: absorber layer with two sintered ferrite panels, each panel having a thickness of 0.2 mm, resulting in a total thickness of 0.4 mm, $\mu'=450$ at 300 kHz and $\mu''<30$ at 300 kHz.

The results set out in FIG. 3 show that the localization error caused by a conductive couch top appears at a couch top to wireless beacon distance of about 20 cm. When the conductive couch top is closer to the beacon and the antenna of transceiver, it causes more loss of electromagnetic field such that the localization error increases to 1.3 cm when the couch top is 3 cm closer to the beacon and transceiver antenna. FIG. 3 also shows that a material with a high $\mu'$ and a low $\mu''$ is suitable for minimizing localization error. In practice, the surface resistance of the absorber layer also affects the electromagnetic field. Although the $\mu$-metal of Case 3 has a very high $\mu'$ it is conductive due to a low surface resistance and is shown to yield a large localization error. Thus, the sintered ferrite material of Cases 5, 6, and 7 is preferred in the present invention. FIG. 3 also shows, with reference to Case 7, that using a multi-layer absorber can further increase the "storage capability" with respect to the electromagnetic field of the ferrite panel, such that the localization error can be further reduced. The overall results shown in FIG. 3 demonstrate that the absorber layer with high $\mu'$, high surface resistance, low $\mu''$ and multi-layer ferrite panels are advantageous for the absorbing device of the present invention.

Further testing of the absorbing device of the present invention was also carried out to consider potential side effects introduced by ferrite materials. For example, the induced radioactivity effect, dose dosimetry change and the potential for X-ray artefacts were considered. The ferrite material used for the absorbing layer of the present invention comprises a set of ceramic compounds composed of iron oxide ($Fe_2O_3$) combined chemically with one or more additional metallic elements, including but not limited to copper oxide (CuO), zinc oxide (ZnO) and nickel oxide (NiO).

Table 1 shows the induced radioactivity (in $\mu Sv$/hour) with different ferrite material compositions. The tests carried out used an 18 MV beam generator to deliver a photon energy of 96 Gy to several ferrite samples. The induced radioactivity was then measured at the surface of the ferrite material samples. It was found that different ferrite material compositions introduce different radioactivity behaviour and that the induced radioactivity decreases to the previous background level after two hours. Further measurement also shows that both $\mu'$ and $\mu''$ do not change after radiation. The impact of induced radioactivity can be reduced by placing the ferrite material of the absorbing layer away from the patient's body. In the present invention, a comfort mattress layer and a spacer layer are introduced above the ferrite material layer/s to minimize such induced radioactivity. It is understood that "above" is in a patient-facing direction away from the couch top surface on which the patient lies.

TABLE 1

| Time after irradiation (minutes) | Sample-1 | Sample-2 | Sample-3 |
|---|---|---|---|
| 0 | 1.8 | 1.6 | 0.8 |
| 10 | 1 | 1 | 0.5 |
| 20 | 0.6 | 0.6 | 0.5 |
| 120 | 0.2 | 0.2 | 0.2 |

Figure 4:
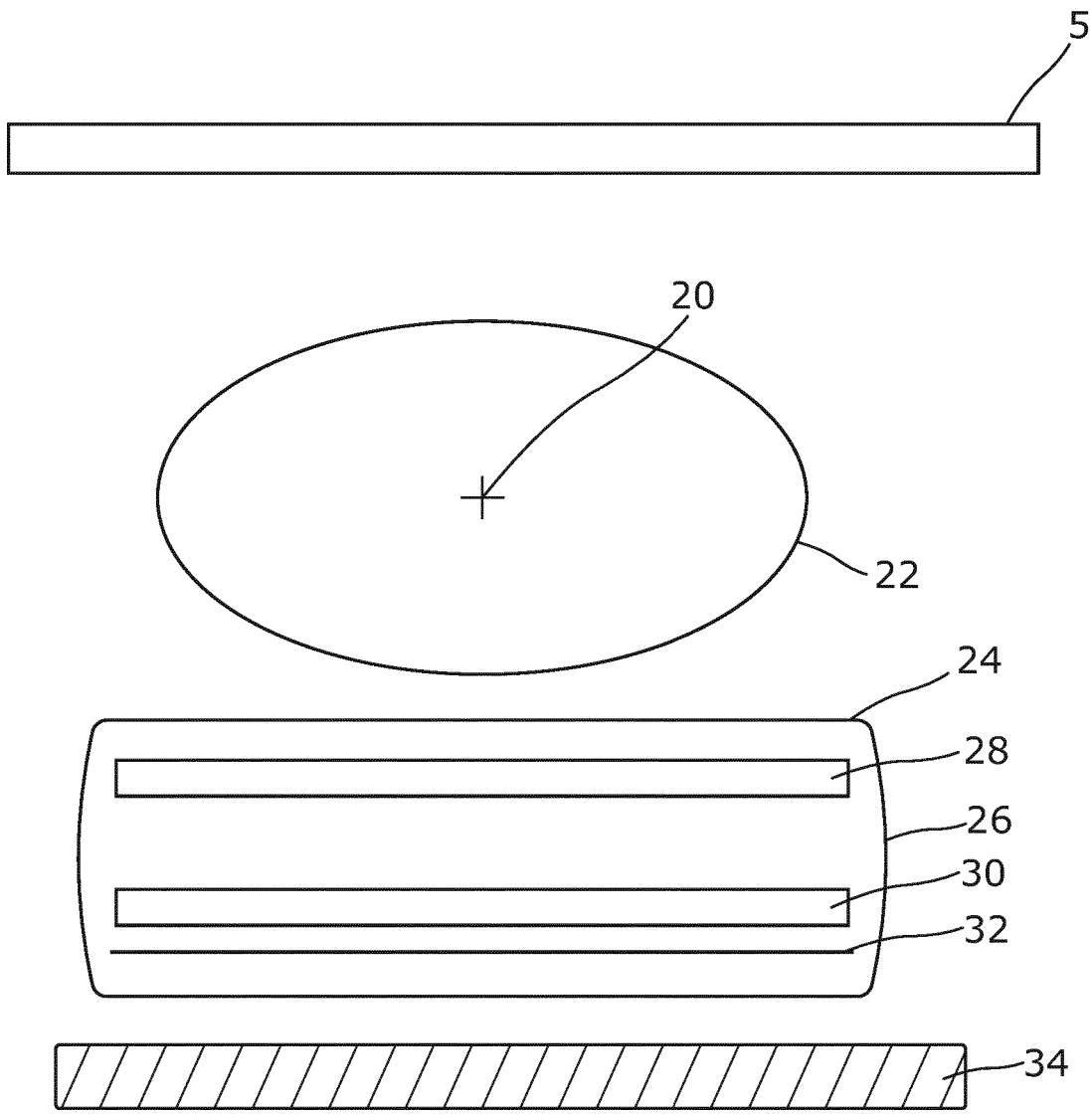
FIG. 4 shows a further schematic cross-sectional view of the device in position between a target and the couch top, showing the additional layers forming the device of a preferred embodiment of the present invention.

Referring to FIG. 4, a simplified schematic of the preferred arrangement of the absorbing device of the present invention is shown. A wireless beacon 20 is shown implanted into the patient 22. During positioning and treatment, the patient 22 lies on the absorbing device 24 of the present invention, which comprises a multi-layer structure. A transceiver and corresponding antenna 5 of the electromagnetic localisation system is placed above or on top of the patient 22. The absorbing device 24 comprises a wrapper 26, which wraps around a comfort mattress layer 28; a spacer layer 30; and an absorber layer 32. The absorbing device 24 of the present invention rests, in use, on—i.e. above the couch top 34. The wrapper 26 may comprise an anti-slip base layer on its couch-facing surface to minimise any movement of the absorbing device 24 when it is placed between the couch top 34 and the patient 22. Alternatively, the wrapper 26 may comprise a means for attaching the absorbing device 24 to the couch top 34 so that it is fixed in place during use. The comfort mattress layer 28 is a padded material, such as foam, or other cushioning material to improve patient comfort. The spacer layer 30 has the advantage of increasing the distance between the patient and the couch top 34, which has been found to further minimise any potential localisation error. The spacer layer 30 may also comprise a reinforcing material to prevent damage to the absorber layer 32, which may be a brittle material.

As previously described, the absorber layer 32 comprises a material having high magnetic permeability to avoid the electromagnetic energy dissipation from the transceiver or wireless beacon that may otherwise introduce localisation errors. The absorber layer 32 also comprises a material having a high surface resistivity to provide a significant resistance to current running along the surface of the couch top 34 and the absorbing device 24. In a preferred embodiment, the absorber layer 32 comprises at least one layer of a sintered ferrite material with high magnetic permeability ($\mu'$), high surface resistivity and low loss ($\mu''$) to absorb magnetic flux generated from the transceiver 5. The absorber layer 32 has the following characteristics:

$\mu'>200$ at 300 kHz;
$\mu''<50$ at 300 kHz;
surface resistance$>1.00E+0.9$ Ohms;
ferrite material composition, comprising at least 50% of iron oxide ($Fe_2O_3$) and, more preferably, also contains Copper oxide (CuO) and/or Zinc oxide (ZnO) and/or Nickel oxide (NiO).

Figure 5:
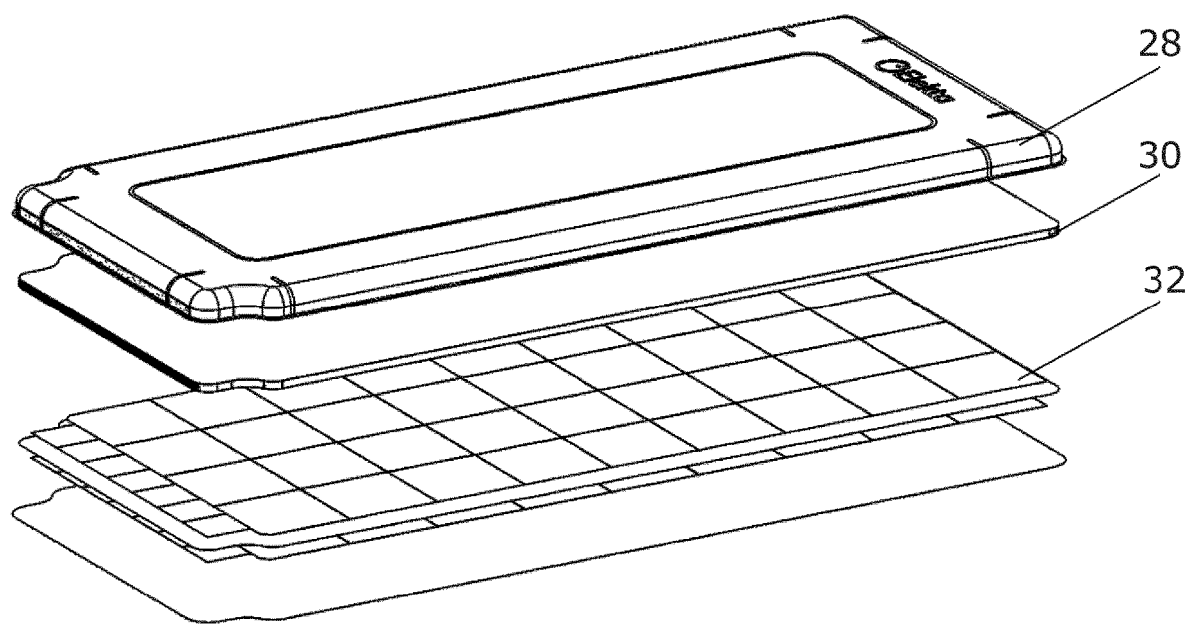
FIG. 5 shows a schematic view of the multiple layers forming the absorbing device of the present invention.

Referring to FIG. 5, the sintered ferrite material used for the absorber layer 32 of the present invention is produced with a thickness of about 0.1 mm. It is envisaged that, in alternative embodiments, the absorber layer has a thickness of about 0.2 mm, about 0.3 mm, or about 0.4 mm. The sintered ferrite material is attached to a sheet of adhesive material having a surface area of 120 mm×120 mm to form a ferrite sheet. This 120 mm×120 mm ferrite sheet is attached to a carrier panel having a greater surface area to form a ferrite panel having the required surface area of about 48 cm×108 cm, which is configured to cover a typical patient's body size. In alternative embodiments, the ferrite sheets are stacked and glued on top of each other to increase the thickness of the ferrite layer.

A multi-layer ferrite panel avoids potential magnetic field saturation due to a large amount of electromagnetic energy generated from the transceiver. As shown in FIG. 5, the absorber layer 32 is separated from the patient, in use, by a mattress layer 28 and a spacer layer 30. It has been found that potential introduction of radioactivity/X-ray artefacts at the surface are avoided by careful arrangement of the mattress and spacer layers 28, 30. The mattress layer 28 and the spacer layer 30 are both non-conductive; have a surface resistance greater than 1.00E+0.9 Ohms; and have very low attenuation of X-rays. The mattress and spacer layers 28, 30 effectively form a "buffer" to minimise or block the induced radioactivity effects and the potential X-ray artefacts generated by the absorber layer 32. The wireless beacons implanted in the patient are further separated from the conductive couch top by the use of the mattress and spacer layers 28, 30 to further improve localisation accuracy.

In alternative embodiments of the present invention, it is envisaged that the absorbing device 24 comprises an absorber layer 32 having a high magnetic permeability but a low surface resistivity, wherein the absorber layer is modified to compensate for the low surface resistivity; for example, by being provided in small pieces surrounded by an insulating medium. It is envisaged that in this configuration the high magnetic permeability/low surface resistivity material would be usable because the material is modified to reduce the electrical conductivity. In one embodiment of the present invention, the absorber layer of the absorbing device comprises plates/tiles of a ferrite material.

Figure 6:
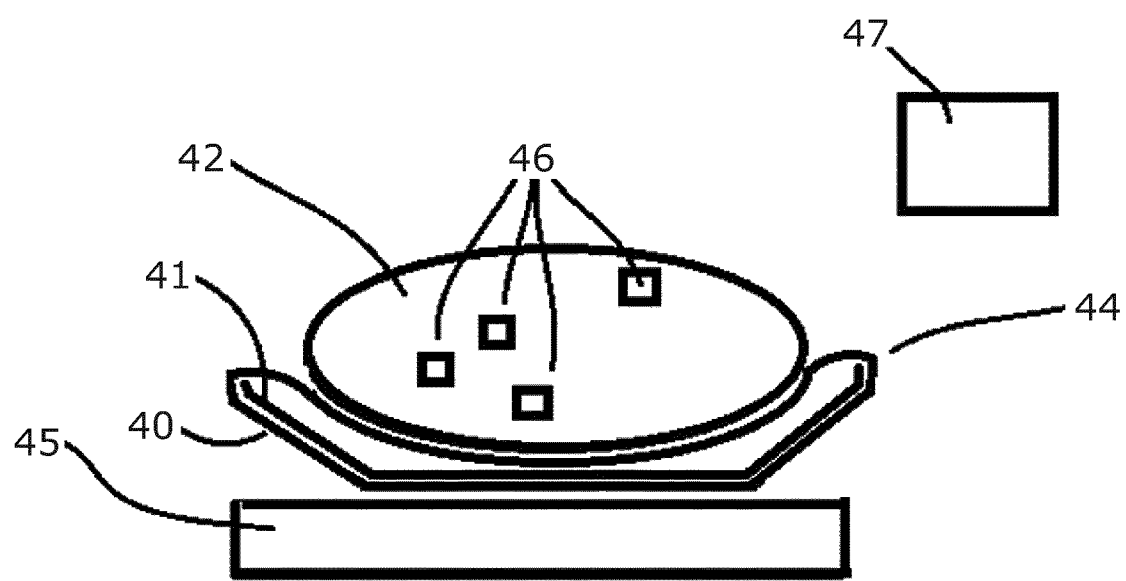
FIG. 6 shows a cross-sectional view of a positioning device comprising the absorbing device of the present invention, positioned between a patient and a treatment couch.
Figure 7:
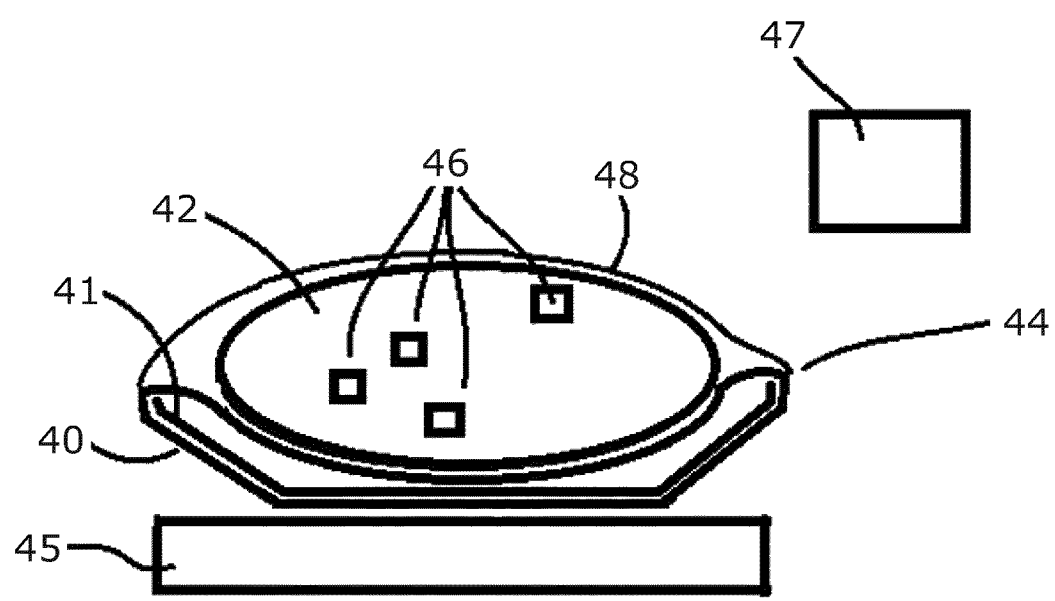
FIG. 7 shows a cross-sectional view of an alternative embodiment of the absorbing device of FIG. 6 positioned between a patient and a treatment couch.

Referring to FIG. 6 and FIG. 7, for reproducible and stable positioning of a patient, a vacuum cushion 40 is used in combination with the absorbing device 41 of the present invention. The vacuum cushion 40 is moulded to the patient's anatomy and allows the patient to be positioned in exactly the same position for imaging and treatment and for each subsequent treatment fraction. Examples are the BlueBAG™ and BodyFIX™ provided by Elekta AB (Publ), which comprises a mouldable vacuum cushion comprising a flexible bag of gas-impermeable material; a flowable filling material such as polystyrene grains or balls; and a valve to allow the bag to be connected to an external vacuum source or a vacuum pump.

The vacuum cushion 40 may also comprise at least one bolster (not shown). For example, the bolster can be shaped to locate a shoulder region of the patient in a comfortable, reproducible position for each treatment fraction; or support the knees of the patient in an elevated position; or be a substantially cylindrical neck roll to support underneath a neck of the patient. The use of additional bolsters or cushions reduces patient movement; improves patient comfort and provides better beam access for treatment, if appropriate. Bolsters or cushions can also be used to allow a patient to hold a "panic button" without introducing unwanted patient movement or increasing patient discomfort.

With reference to FIG. 6, prior to imaging or treatment, a positioning device 44 is vacuum-moulded to a couch-facing part of a patient 42, or to the entire body of the patient 42. The positioning device 44 is placed on a couch 45 and may be fixed thereto; for example at successive indexed fixing points along the couch top. The couch 45 and positioning device 44 are releasably fixed together; for example using a releasable, elongated bar with two pins projecting to be received in corresponding holes in the positioning device 44; or the positioning device 44 is releasably fixed to the couch 45 using a hook and loop fastener, such as Velcro™, or similar. It is envisaged that the positioning device 44 covers substantially all and/or overlaps the couch top, such that the width of the positioning device 44 is equal to or greater than the width of the couch 45. In alternative embodiments, the positioning device 44 is moulded only to a required body region of the patient 42 and so only shields the couch 45 in that region.

Referring to FIG. 6, a patient 42 is placed on the positioning device 44, which is placed on the treatment couch 45, with the positioning device 44 in an inflated, soft and mouldable state.

With the patient 42 resting on the positioning device 44 and lying in the desired position, the vacuum cushion 40 of the positioning device 44 is connected to a vacuum source or a vacuum pump (not shown) and the gas contained therein is evacuated to compress the filling material and prevent any further movement of the filling or the positioning device 44. Thus, the patient 42 is held by the moulded vacuum cushion 40 of the positioning device 44 in a reproducible position. The vacuum cushion 40 of the patient positioning device 44 is held in a substantially rigid state until the vacuum is broken and the positioning device 44 is returned to a soft and mouldable state to allow the patient to dismount the couch 45.

As previously described, to allow for patient localisation one or more wireless beacons 46 are positioned in, on or adjacent to the patient 42. The absorbing device 41 of the present invention is incorporated within the positioning device 44 and prevents the introduction of localisation errors in the calculation of the location of the treatment target caused by the surrounding conductive materials and electromagnetic noise. An electromagnetic transceiver 47 is positioned for communication with the wireless markers 46 to allow identification and/or accurate, undistorted positional information to be detected. The transceiver 47 is held in a fixed position or is moveable using a robotic arm (not shown) to move the transceiver 47 into a desired position with respect to the wireless beacons 46 that are to be detected.

Referring to FIG. 7, in an alternative embodiment of the present invention, the patient positioning device 44 further comprises a plastic cover sheet 48. A patient 42 is placed on the positioning device 44, as previously described, and the patient 42 is covered by the transparent plastic cover sheet 48, which is adhesively secured to the positioning device 44 around its perimeter; or at least along two opposing edges of the positioning device 44. The transparent plastic cover sheet 48 allows a patient 42 to be seen through the sheet and is also transparent to wireless signals.

As previously described, with the patient 42 resting on the positioning device 44 and lying in the desired position, the vacuum cushion 40 of the positioning device 44 is connected to a vacuum source or a vacuum pump (not shown) and the gas contained therein is evacuated to compress the filling material and prevent any further movement of the filling or the positioning device 44. In this alternative embodiment, the patient 42 is held by the moulded vacuum cushion positioning device 44 and by the transparent plastic cover sheet 48 in a reproducible position. Both the vacuum cushion 40 and the cover sheet 48 are held in a substantially rigid state until the vacuum is broken. The positioning device 44 is returned to a soft and mouldable state to allow the patient 42 to dismount the couch 45.

The positioning device of the present invention can be provided to mould to and position the whole of the patient's body; or be provided for a specific body part or region, such as the hip or thorax. It is envisaged that after treatment the plastic sheet 48 can be removed and replaced and the positioning device 44 can be re-inflated and used for positioning of another patient 42.

The present invention further optimises the mass density and thickness of the absorber layer that is used. A higher mass density and a thicker ferrite absorber layer have been found to result in a greater impact on the dose dosimetry profile. These factors are carefully controlled during manufacture of the absorbing device of the present invention. The present invention also takes into account that different ferrite material compositions result in different attenuation of X-ray imaging. The risk of introducing X-ray artefacts is carefully considered and the nature of the material and the number of ferrite layers used is determined accordingly. For example, an image contrast change at 10.1 mm above the surface of the couch top was introduced when using a single-layer of ferrite material having a thickness of 0.3 mm; whereas, the image contrast change is introduced at 50.0 mm above the surface of the couch top when a laminar absorbing device having five, stacked ferrite panels is used, each having a thickness of 0.3 mm and so a total thickness of 1.5 mm.

In a further embodiment of the present invention, shown in FIG. 8a, further electromagnetic shielding is also provided around the patient body to allow for any further sources of electromagnetic noise; for example, from surrounding conductive materials. The transceiver antenna 5', which in use is above the patient body (not shown), is shielded by an absorbing device 24' above the transceiver antenna 5'. As before, "above" is understood to be the opposing direction to the couch top 4, on which the patient lies. The absorbing device 24' comprises both lateral and transverse panels, which in use form a frame around the patient (not shown). The absorbing device 24' is an open cuboidal shape allowing the patient's body to pass into and/or through the absorbing device, when supported by the couch top 4 as shown in FIG. 8b. Alternatively, as shown in FIG. 8c, the absorbing device 24" can comprise a single panel above the transceiver antenna 5'.

In a further aspect of the present invention, as an alternative or in addition to the pad or mattress accessory solution previously described, the absorbing device of the present invention can be integrated into a couch top or permanently fixed thereto. Thus, the present invention provides a combined solution whereby a carbon couch top is combined with the absorbing device, to offer a solution that is transparent to X-ray radiation; i.e. with very low X-ray attenuation, and maintains the electromagnetic field strength of a localisation system without disconnecting magnetic flux.

As previously described, the integrated couch top of the present invention comprises an absorber layer combined with an insulation layer. In use, with a patient lying on the couch top, the patient is not directly contacting the absorber layer but is separated therefrom by a non-conductive insulation layer, having a surface resistance greater than 1.00 E-0.9 Ohms. This minimises the induced radioactivity effects and blocks any potential X-ray imaging artefacts generated by the absorber layer. As described with respect to other aspects of the present invention, the insulation layer comprises any one or more of the following materials: epoxy, polyester, polymer, polymethacrylimide, vinyl ester resin, wood, ceramic, aramid, glass fibre or ultrahigh molecular weight polyethylene. The insulation layer provides additional reinforcement to the carbon fibre couch top, increasing the rigidity and loading capacity of the couch top. Furthermore, the insulation layer may comprise a non-conductive foam to act as cushioning and improve patient comfort.

The integrated couch top comprises an absorber layer having a least one ferrite panel with high magnetic permeability, wherein the real part of relative permeability ($\mu'$) is greater than 200 at 300 kHz and the imaginary part of relative permeability ($\mu''$) is less than 50 at 300 kHz. It is to be understood that the magnetic permeability and the material selected can be further optimised according to the applied magnetic field. The ferrite material used for the absorbing layer of the present invention comprises a set of ceramic compounds composed of iron oxide ($Fe_2$; $O_3$); preferably with at least 50% of total ferrite material mass. In further preferred embodiments, the material of the absorber layer is also combined chemically with one or more additional metallic elements, including but not limited to copper oxide (CuO), zinc oxide (ZnO) and nickel oxide (NiO).

The integrated couch top comprises an absorber layer having a plurality of ferrite sheets; wherein each ferrite sheet has a relatively small size of about 60 cm×60 cm and thickness of between about 0.1 mm and 1 mm. Prior to integrating the absorber layer into the couch top, the ferrite sheet is pre-assembled on an adhesive layer to form a larger panel. Preferably, the larger ferrite sheet is supported by a reinforcing layer. For example, the reinforcing carrier layer is rigid and comprises a conductive material, such as carbon fibre, which has very low X-ray attenuation. In alternative embodiments of the integrated couch top, the thickness of the absorber layer is adjusted according to requirements, with stacking of ferrite panels and/or layers to form a thicker layer if required.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

Appendix

In addition to FIGS. 1 to 8; further evidence to demonstrate the novel approach of using a mattress and a spacer layer as a buffer to remove X-ray imaging artefacts is demonstrated in comparison with existing prior-art devices.

FIG. 9 illustrates the introduced X-ray artefacts on a head phantom with different ferrite samples. The X-ray imaging is acquired after passing through different ferrite samples. It shows that artefacts are dependent on material composition. The final ferrite material composition is the optimized embodiment described with respect to the present invention. The proposed solution using ferrite material has the potential to introduce X-ray artefacts and seriously limit the clinical usage with LINAC applications. FIG. 9a—no ferrite sample; FIG. 9b—ferrite sample 1; FIG. 9c—ferrite sample 2; FIG. 9d—ferrite sample 3.

FIG. 10. is an illustration of the X-ray artefacts with multi-layer ferrite panels: (a) single layer ferrite panel; (b) five-layer ferrite panels FIG. 10a illustrates that the image contrast change at 10.1 mm above the couch top is introduced by a single-layer ferrite panel. Having a thickness of 0.3 mm. FIG. 10b illustrates that the image contrast change increases to 50.0 mm above the couch top with stacking five layer ferrite panels, having a thickness of 5×0.3 mm, with the panels stacked on top of each other. The applicant has shown that the ferrite layer introduces X-ray artefacts and the artefacts become worse with more layers. To solve this, the present applicant introduced the use of a mattress layer and a spacer layer, which act as a buffer to effectively "push"; i.e. to effectively move the patient's body further away from the ferrite layer, such that there are no X-ray artefacts presented at the targeted body part.

The invention claimed is:

1. A mattress for radiotherapy treatment comprising an absorbing device for radiotherapy treatment comprising at least one layer of electromagnetic absorbing material,
    wherein the absorbing material is for preventing interaction between a target localisation system having a targeted frequency range of between about 300 kHz and 500 kHz and a treatment table,
    wherein the absorbing device comprises a ferrite layer and at least one spacer layer positioned above the ferrite layer in a patient-facing direction away from the couch top surface on which the patient lies;
    wherein the ferrite layer comprises a plurality of sheets of a sintered ferrite material.

2. The mattress according to claim 1, further comprising a comfort mattress layer positioned above the ferrite layer in a patient-facing direction away from the couch top surface on which the patient lies.

3. The mattress according to claim 1 wherein the absorbing device comprises an absorber layer comprising a material having high magnetic permeability, wherein the real part of relative permeability ($\mu'$) is greater than 200 at 300 kHz and the imaginary part of relative permeability ($\mu''$) is less than 50 at 300 kHz.

4. The mattress according to claim 1 wherein the absorbing device comprises an absorber layer having surface resistivity greater than 1.00E+0.9 Ohms.

5. The mattress according to claim 3 wherein the absorber layer comprises a plurality of stacked sintered ferrite sheets.

6. The mattress according to claim 1 wherein the sintered ferrite material comprises iron oxide ($Fe_2O_3$); preferably, wherein at least 50% of the total mass of the sintered ferrite material comprises iron oxide ($Fe_2O_3$); and/or wherein the ferrite material further comprises at least one of Nickel Oxide (NiO); and/or Zinc Oxide (ZnO); and/or Copper Oxide (CuO).

7. The mattress according to claim 1 wherein each sheet of sintered ferrite material has a thickness of between 0.1 mm and 1 mm.

8. The mattress according to claim 1 having a plurality of partially overlapping sheets.

9. The mattress according to claim 1 wherein each sheet is attached to at least one layer of adhesive; preferably, to at least one layer of an adhesive tape.

10. The mattress according to claim 1 wherein the spacer layer includes a reinforcing material such as epoxy, and/or polyester, and/or polymer, polymethacrylimide, and/or vinyl ester resin, and/or wood, and/or ceramic, and/or aramid, and/or glass fibre, and/or ultrahigh molecular weight polyethylene.

11. An absorbing device for radiotherapy treatment, comprising at least one layer of electromagnetic absorbing material, wherein the absorbing material is for preventing interaction between a target localisation system having a targeted frequency range of between about 300 kHz and 500 kHz and a treatment table,
    wherein the absorbing device comprises a ferrite layer,
    wherein the ferrite layer comprises a plurality of sheets of a sintered ferrite material, and
    wherein the absorbing device is for positioning around a patient.

12. The absorbing device according to claim 11 wherein the absorbing device comprises at least two upstanding walls and at least one transverse member therebetween for positioning over and around a patient.

13. A couch top for patient support for radiotherapy treatment comprising a mattress according to claim 1.

14. A couch top for patient support for radiotherapy treatment comprising a mattress according to claim 11.

\* \* \* \* \*